US012708681B2

(12) United States Patent
Opie

(10) Patent No.: US 12,708,681 B2
(45) Date of Patent: Aug. 18, 2026

(54) METHOD OF STERILIZATION SPECIMEN CONDITIONING

(71) Applicant: Noxilizer, Inc., Hanover, MD (US)

(72) Inventor: David Opie, Hanover, MD (US)

(73) Assignee: Noxilizer, Inc., Hanover, MD (US)

( * ) Notice: Subject to any disclaimer, the term of this patent is extended or adjusted under 35 U.S.C. 154(b) by 445 days.

(21) Appl. No.: 18/334,170

(22) Filed: Jun. 13, 2023

(65) Prior Publication Data

US 2023/0405159 A1 Dec. 21, 2023

Related U.S. Application Data

(60) Provisional application No. 63/352,117, filed on Jun. 14, 2022.

(51) Int. Cl.
*A61L 2/06* (2006.01)
*A61L 2/26* (2006.01)

(52) U.S. Cl.
CPC .................. *A61L 2/06* (2013.01); *A61L 2/26* (2013.01); *A61L 2202/122* (2013.01); *A61L 2202/14* (2013.01)

(58) Field of Classification Search
CPC . A61L 2/0023; A61L 2/04; A61L 2/06; A61L 2/26; A61L 2202/122; A61L 2202/14; A61L 2202/24; A23B 2/10; A23B 2/103; A23B 2/70; A23B 2/708; A23B 2/721; A23B 2/80
See application file for complete search history.

(56) References Cited

U.S. PATENT DOCUMENTS 4,203,943 A * 5/1980 Gillis ...................... A61L 2/206 422/111
4,457,892 A * 7/1984 Young ..................... A61L 2/206 422/2

(Continued)

FOREIGN PATENT DOCUMENTS

CN 204193116 U 3/2015
JP 2014079301 A 5/2014

(Continued)

OTHER PUBLICATIONS

Invitation to Pay Additional Fees and, Where Applicable, Protest Fee for International Application No. PCT/US2023/068363, mailing date Oct. 2, 2023.

(Continued)

*Primary Examiner* — Jennifer Wecker
*Assistant Examiner* — Brady C Pilsbury
(74) *Attorney, Agent, or Firm* — COOLEY LLP

(57) ABSTRACT

Methods and systems for modifying a temperature of a product to be sterilized while the product is in a sterilization chamber. Temperature modification may be achieved through air circulation, through manipulation of a temperature of one or more walls of the sterilization chamber, and/or through manipulation of pressure within the sterilization chamber. Using the capabilities of the sterilization chamber to accelerate product warming may reduce the time required to warm a product to be sterilized from a refrigerated state to a temperature at which sterilization is to be performed. After sterilization, the product may also be cooled in the sterilization chamber.

15 Claims, 5 Drawing Sheets

(56) References Cited

U.S. PATENT DOCUMENTS

| | | | | |
|---|---|---|---|---|
| 4,759,909 | A * | 7/1988 | Joslyn | A61L 2/06 422/26 |
| 6,046,243 | A | 4/2000 | Wellinghoff et al. | |
| 6,325,972 | B1 | 12/2001 | Jacobs et al. | |
| 6,365,102 | B1 | 4/2002 | Wu et al. | |
| 7,045,096 | B2 | 5/2006 | D'Ottone | |
| 7,695,673 | B2 | 4/2010 | Moisan et al. | |
| 8,017,074 | B2 | 9/2011 | Arnold et al. | |
| 8,062,590 | B1 * | 11/2011 | Ricciardi | A61L 2/20 134/131 |
| 8,252,228 | B1 | 8/2012 | Freeman et al. | |
| 8,252,229 | B2 | 8/2012 | Thomas et al. | |
| 8,425,837 | B2 | 4/2013 | Carbone et al. | |
| 8,425,852 | B2 | 4/2013 | Matsuuchi et al. | |
| 8,580,086 | B2 | 11/2013 | Matsuuchi et al. | |
| 8,703,066 | B2 | 4/2014 | Vaughn et al. | |
| 8,703,666 | B2 | 4/2014 | Tsou et al. | |
| 8,721,984 | B2 | 5/2014 | Carbone et al. | |
| 8,802,006 | B2 | 8/2014 | Thomas et al. | |
| 8,808,622 | B2 | 8/2014 | Arnold et al. | |
| 8,968,651 | B2 | 3/2015 | Hayashi et al. | |
| 9,101,679 | B2 | 8/2015 | Robitaille et al. | |
| 9,180,217 | B2 | 11/2015 | Arnold et al. | |
| 9,474,815 | B2 | 10/2016 | Dufresne et al. | |
| 9,655,987 | B2 | 5/2017 | Hayashi et al. | |
| 9,731,041 | B2 | 8/2017 | Akutsu | |
| 9,814,795 | B2 | 11/2017 | Dufresne et al. | |
| 10,314,929 | B2 | 6/2019 | Nowruzi et al. | |
| 10,335,507 | B2 | 7/2019 | Reed et al. | |
| 10,383,966 | B2 | 8/2019 | Dufresne et al. | |
| 10,398,796 | B2 | 9/2019 | Shomali et al. | |
| 10,532,118 | B2 | 1/2020 | Reed et al. | |
| 10,647,461 | B2 | 5/2020 | Altmann et al. | |
| 10,787,285 | B2 | 9/2020 | Linnestad | |
| 10,806,850 | B2 | 10/2020 | Patel et al. | |
| 11,097,029 | B2 | 8/2021 | Dufresne et al. | |
| 11,224,555 | B2 | 1/2022 | Chudek et al. | |
| 11,813,426 | B2 | 11/2023 | Forster et al. | |
| 2008/0317626 | A1 | 12/2008 | Arnold et al. | |
| 2011/0274583 | A1 | 11/2011 | Hayashi et al. | |
| 2013/0004380 | A1 | 1/2013 | Yoo | |
| 2019/0224356 | A1 | 7/2019 | Nowruzi et al. | |
| 2019/0314535 | A1 * | 10/2019 | Golkowski | A61L 2/208 |
| 2020/0101186 | A1 | 4/2020 | Shodder | |
| 2020/0171244 | A1 * | 6/2020 | Weikart | C23C 16/5093 |
| 2020/0306401 | A1 | 10/2020 | Cookson et al. | |
| 2020/0338271 | A1 | 10/2020 | Harris et al. | |
| 2021/0060258 | A1 | 3/2021 | Mismar et al. | |
| 2021/0077645 | A1 | 3/2021 | Mismar et al. | |
| 2021/0228797 | A1 | 7/2021 | Janke et al. | |
| 2021/0261297 | A1 * | 8/2021 | Bitong | A61M 5/008 |
| 2021/0299306 | A1 | 9/2021 | Takahashi et al. | |
| 2022/0160972 | A1 | 5/2022 | Chou et al. | |
| 2022/0331470 | A1 * | 10/2022 | Shodder | A61L 2/24 |
| 2023/0043679 | A1 | 2/2023 | Moberg et al. | |
| 2023/0364286 | A1 | 11/2023 | Opie | |
| 2023/0404850 | A1 | 12/2023 | Chou et al. | |
| 2023/0405159 | A1 | 12/2023 | Opie | |

FOREIGN PATENT DOCUMENTS

| | | | |
|---|---|---|---|
| JP | 2014094302 | A | 5/2014 |
| KR | 1020180112142 | A | 10/2018 |
| WO | 2018217995 | A1 | 11/2018 |
| WO | 2020263986 | A1 | 12/2020 |
| WO | WO-2021056020 | A1 | 3/2021 |
| WO | WO-2023220384 | A1 | 11/2023 |
| WO | WO-2023245012 | A1 | 12/2023 |

OTHER PUBLICATIONS

Fujiwara et al., "Chemical-Gas Sterilization of External Surface of Polymer-Based Prefilled Syringes and Its Effect on Stability of Model Therapeutic Protein," Journal of Pharmaceutical Sciences, pp. 1-10, 2021. Accepted Sep. 2, 2021.

Invitation to Pay Additional Fees dated Aug. 25, 2023 for International Application No. PCT/US2023/022604.

CA Application No. 3257084, Office Action mailed Dec. 2, 2025; Applicant Noxilizer, Inc., 4 total pages.

PCT Application No. PCT/US2023/022064, International Preliminary Report on Patentability mailed Nov. 28, 2024, Applicant Noxilizer, Inc.; 14 pages.

PCT Application No. PCT/US2023/022064, International Search Report and Written Opinion mailed Oct. 18, 2023, Applicant Noxilizer, Inc.; 18 pages.

PCT Application No. PCT/US2023/022064, Invitation to Pay Additional Fees mailed Aug. 25, 2023 Applicant Noxilizer, Inc.; 12 pages.

PCT Application No. PCT/US2023/068363, International Preliminary Report on Patentability mailed Dec. 26, 2024, Applicant Noxilizer, Inc.; 12 pages.

PCT Application No. PCT/US2023/068363, International Search Report and Written Opinion mailed Nov. 24, 2023, Applicant Noxilizer, Inc.; 16 pages.

U.S. Appl. No. 18/316,681, Non-Final Office Action mailed Mar. 9, 2026; Inventor Opie, David.; 21 pages.

* cited by examiner

METHOD OF STERILIZATION SPECIMEN CONDITIONING

CROSS REFERENCE TO RELATED APPLICATIONS

The present application claims the benefit of and priority to US Provisional Pat. App. 63/352,117, filed Jun. 14, 2022, titled METHOD OF STERILIZATION SPECIMEN CONDITIONING, the disclosure of which is incorporated herein by reference.

BACKGROUND

A wide range of products can be sterilized in a variety of ways including using moist heat (steam), dry heat, radiation, ethylene oxide gas, vaporized hydrogen peroxide, chlorine dioxide gas, vaporized peracetic acid, and nitrogen dioxide. Some products to be sterilized need to be maintained at specific temperatures to avoid product degradation. For example, some biologic products may be stored at temperatures below room temperature. In some examples, a biologic product may be packaged in a pre-filled syringe which must itself be refrigerated. However, the pre-filled syringe still needs to be sterilized prior to shipping to users.

To sterilize refrigerated products one approach is to allow the product to warm to room temperature for 1-2 days before sterilization. This introduces a significant period of delay in the process, and also subjects the products to conditions that are outside of the desired storage temperature range, possibly degrading product or accelerating degradation thereof. New and alternative approaches that can reduce the time that the product is outside of the storage temperature range for sterilization are desired.

OVERVIEW

The present inventors have recognized, among other things, that a problem to be solved is the need for new and/or alternative methods for pre-processing products to be sterilized. In various illustrative examples, a product to be sterilized is taken from a temperature-controlled environment, such as a refrigerated space, and placed in a sterilization chamber. The product to be sterilized does not need to be warmed prior to placement in the sterilization chamber. Product to be sterilized may be partly warmed during the process of removal from storage and placement in the sterilization chamber, for example, due to the time required for such steps.

Once in the sterilization chamber, one or more pre-sterilization cycles are used to warm the product to be sterilized more quickly than could occur if the sample were simply placed on a pallet and allowed to warm to room or other temperature. The pre-sterilization cycles may include the application of a vacuum to the sterilization chamber to extract gas therefrom, followed by introduction of a gas to the sterilization chamber to increase the temperature therein, accelerating warming of the product to be sterilized. The pre-sterilization cycles may be performed without using any sterilant in some examples. The pre-sterilization cycles may use any suitable gas, including but not limited to dry air. Humidity or other gas may be introduced to the chamber to accelerate the warming process.

In further examples, a product that has been sterilized in a sterilization chamber is also cooled in the sterilization chamber during a period of post-sterilization purging and aeration cycles. Cooling may be induced by cooling the chamber walls and/or circulating cooled air in the chamber. Cooling may also be induced by the use of pressure cycling, if desired.

This overview is intended to introduce the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
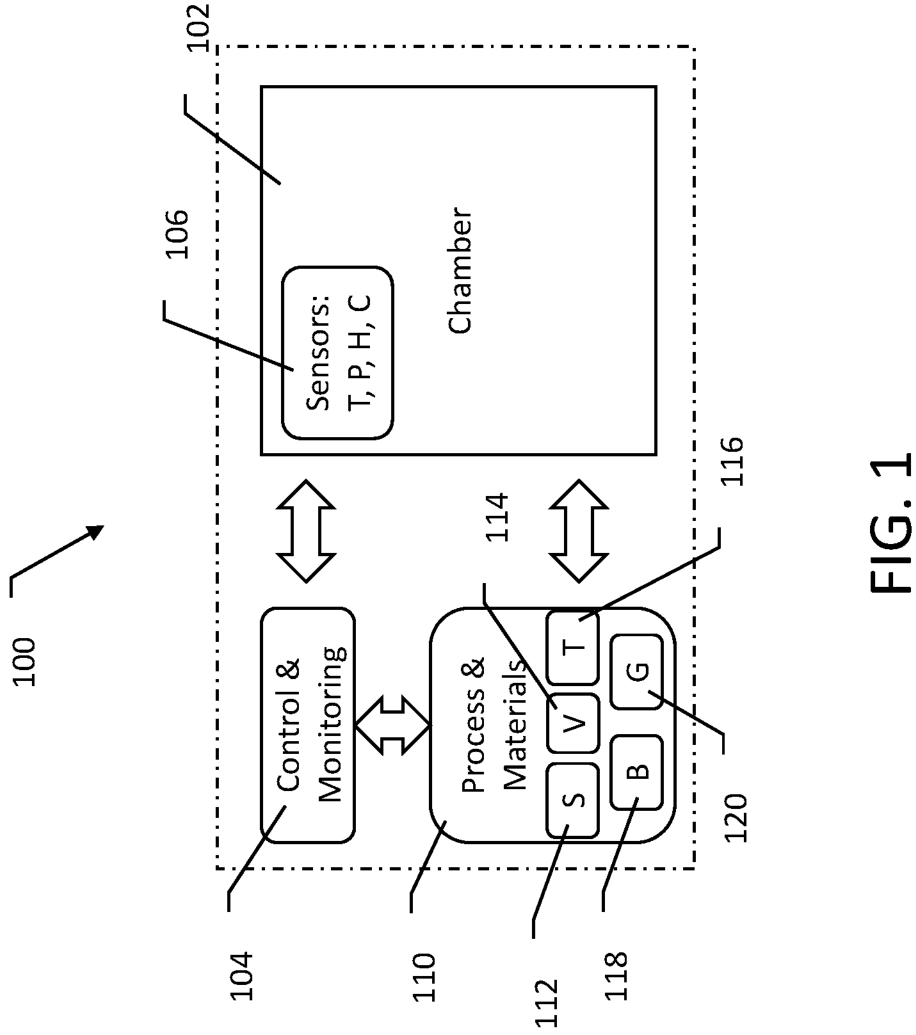
FIG. 1 shows a sterilization apparatus in block form.

FIG. 1 shows a sterilization apparatus in block form. The apparatus 100 may take a range of sizes, from industrial versions that take up entire rooms at a plant, with volumes in the thousands of liters, down to portable version that may be used in the healthcare setting such as a hospital, with volumes in the tens to hundreds of liters. The apparatus 100 includes a sterilization chamber 102, typically an enclosure having a door that can be sealed for airtightness.

A control and monitoring system is included at 104 and may include a microprocessor(s), microcontroller(s), user interface, memory, various sensing, measuring, conditioning, and communication circuits, as needed. For example, control and monitoring 104 may include a graphical user interface (a screen, whether touch or not), a keyboard/mouse/touchscreen or other data/command entry station, a processor such as a microprocessor or microcontroller having associated memory for performing methods as disclosed herein and others known in the art. The control and monitoring system 104 may take a range of different forms.

The control and monitoring system 104 is coupled (such as by wire, optical or wireless connection) to the chamber 102 to obtain various data from sensors 106 therein, which sensors 106 may include temperature, pressure, humidity, chemical and/or other sensors. The specific sensors may vary with the particular sterilization chemistry or process being used. Typically redundant sensors are provided in a chamber 102, though this does not have to be the case. For example, plural temperature or humidity sensors 106 may be distributed throughout the chamber 102.

The sterilization process is controlled by the control and monitoring block 104 using the process and materials technology 110 that is available. These may include, for example, a sterilant source 112 (sometimes a pressurized canister holding a sterilant but not necessarily), a vacuum source 114, a temperature control apparatus 116, a blower 118, and other gas sources 120. The sterilant 112 may be any suitable sterilant, including but not limited to steam, ethylene oxide, nitrogen dioxide, hydrogen peroxide, chlorine dioxide, vaporized peracetic acid, for example. A vacuum 114 may be applied using any suitable vacuum pump design (liquid ring, rotary vane, running claw, etc.). Temperature control apparatus 116 may include, in various forms, a resistive heating apparatus, a Peltier cooling apparatus, a refrigeration system, and/or the use of piping in or on the walls of the chamber 102 through which heated or cooled fluid is pumped. A blower 118 can be provided to circulate the gasses within the chamber, ensuring mixing of gasses and preventing localized concentrations and condensation. Additional gas sources 120 can be provided as well, including in particular non-sterilant gas sources such a sources of water vapor and/or dry air, or other particular gasses (nitrogen, oxygen, as well as inert gasses, as desired).

Figure 2:
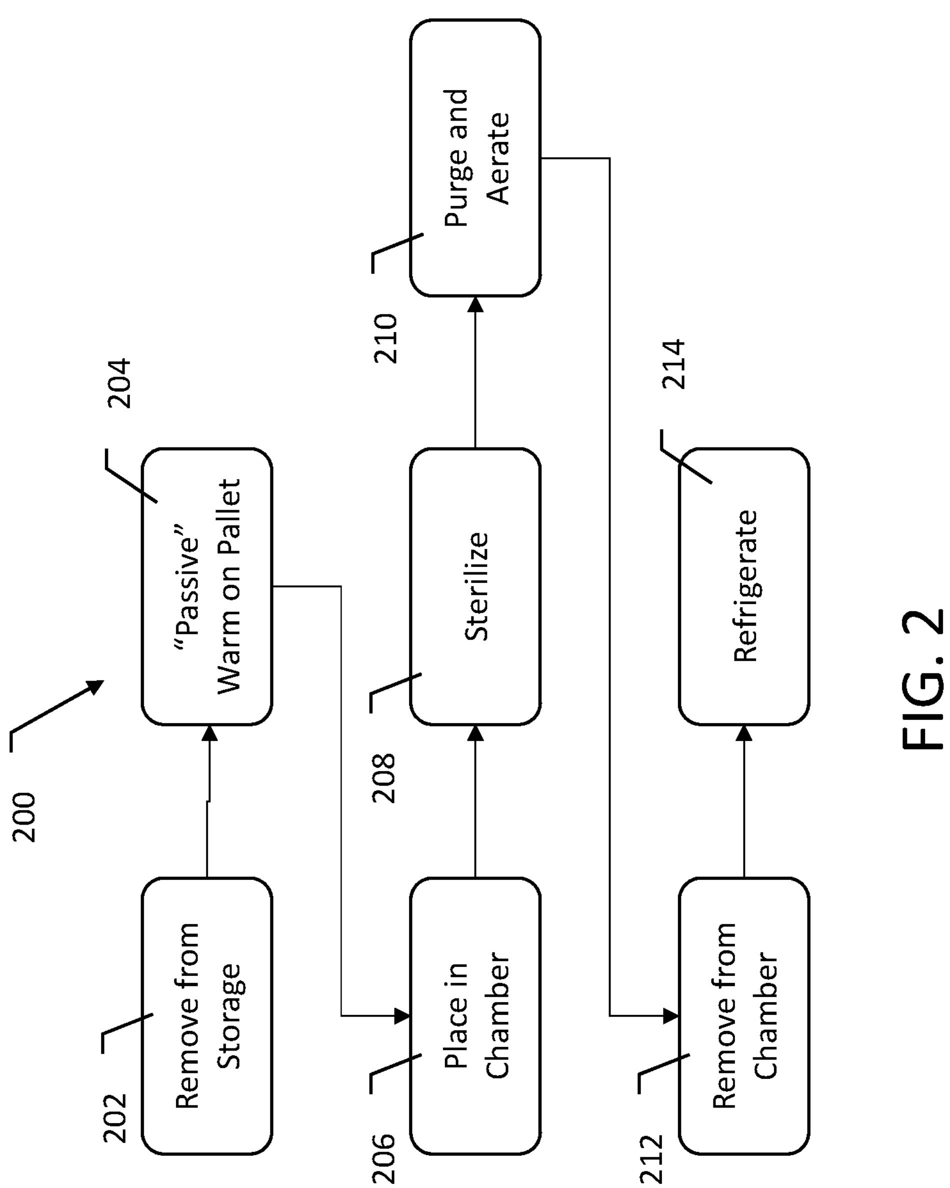
FIG. 2 shows an illustrative prior sterilization process.

A prior art sterilization process is shown in block form in FIG. 2. The method 200 starts with removal of the product to be sterilized from storage at 202. In some examples, the storage at 202 may be a refrigerated location, as various drugs, biologics, and devices can be stored at cool temperatures to, for example, prevent degradation thereof.

Starting a sterilization process with the product to be sterilized at a cold temperature, relative to the rest of the sterilization chamber, may create difficulties. For example, cold product may be subject to condensation of the sterilant and/or other gaseous products (humidity/water vapor) in the chamber on or adjacent to the product to be sterilized. Once condensed, the sterilant may not be functional as a sterilization agent, and may cause chemical reactions introducing undesired contaminants, which may be toxic, in the chamber. Moreover, sterilization processes are typically validated using controlled conditions, including placing the devices to be sterilized in the chamber while at room temperature (approximately in a range of about 18-24 C).

While some sterilization processes (NO2) may be performed at temperatures below room temperature, this is not always the case, and the process parameters for such "cold" sterilization may be burdensome (for example, overlong cycle times) or create other difficulties (such as condensation). For this reason, the prior art process includes passively warming the product to be sterilized on a pallet, as indicated at 204. This step 204 is referred to here as "passive" insofar as the pallet is simply placed in a room and allowed to warm by convection. It is common for step 204 to require 24 to 72 hours, or longer. This not only slows the entire sterilization process, it subjects at least some of the product to a long period of time at a temperature known to cause degradation. For example, product near the outside of the pallet is likely to warm to room temperature rapidly, within hours, and sits at this room temperature for the rest of the period while product in the middle of the pallet slowly warms up.

Once the product is warmed at 204, the product is placed in the sterilization chamber 206, and sterilized 208 using whatever specific process the particular sterilant requires. Next the chamber is purged and the product is aerated at 210. Multiple iterations of the sterilization process 208 and/or purge and aerate 210 may be performed. Sometimes the (final) aeration process can extend for hours. The product is then removed from the chamber at 212; in some instances, aeration occurs both before and after removal from the chamber at 212. The product is then returned to storage/refrigeration at 214.

In many instances, the sterilization process 208 begins with a series of steps that pre-condition the product sample and/or sterilization chamber. For example, the chamber and product may be dried or humidified (or dried then humidified). The present inventor has recognized that these pre-conditioning processes provide an opportunity to shorten the time spent warming the product after removal from storage.

The Ideal Gas Law states:

$$P*V=n*R*T$$

Where P is pressure, V is volume, n is the quantity of molecules of the gas, R is a constant, and T is temperature. For purposes herein, the ideal gas law is sufficient to approximate actual process effects. In a closed chamber, extracting a quantity of the enclosed gas will result in reducing both temperature and pressure, and injecting a quantity of external gas will increase both temperature and pressure. The kinetics of the gas will determine the actual changes in pressure and temperature and how the system returns to eventual equilibrium.

If a quantity of products at a relatively cold temperature are placed in a sterilization chamber that is at a relatively warmer temperature, and the chamber is sealed and thermally isolated, eventually an equilibrium will be reached. The chamber walls will not typically be thermally isolated, and instead are continuously thermally affected by their surroundings, even absent active heating/cooling processes. Because the mass of the sterilization chamber walls will typically exceed (by a factor of, for example, 10) mass of the product to be sterilized, the resulting temperature will be closer to the initial temperature of the sterilization chamber walls.

In some examples, processes of heating and/or cooling may be further accelerated by warming or cooling the chamber walls using an active heating or cooling process. One example is achieved by providing piping in/on chamber walls and circulating a warming or cooling fluid through the piping. Other examples may provide heating or cooling by contact with resistive heating elements or cooling devices such as an evaporator.

In some examples, a product to be sterilized may be placed in the sterilization chamber, with the product in cold state (whether directly from a refrigerated location or at least partly warmed prior to introduction to the sterilization chamber). In the existing process of passive warming, a pallet of products would typically be placed on a pallet and wrapped in plastic to prevent contamination by dust, dirt, bugs, etc., as the pallet warms in ambient air. The plastic wrapping limits or reduces airflow and slows warming significantly, turning entrapped air into an insulator that maintains the cold temperature of the product. The sterilization chamber, on the other hand, is readily sealed and clean inside. Thus the product can be transferred to the sterilization chamber after removal of any extra plastic wrapping or other secondary packaging (a paper or plastic box, for example). Once in the sterilization chamber, the chamber blower can be activated to provide airflow through the pallet, accelerating warming. In addition, if desired, the walls of the sterilization chamber may be actively warmed to or above room temperature as the blower is used, and/or circulating air may be heated, to accelerate warming.

In some examples, to transfer heat to the products to be sterilized more rapidly, a series of chamber evacuation and fill steps can be performed. Product to be warmed and sterilized can be introduced to the chamber, and the chamber can then be sealed. At this point, the pressure in the chamber will be the ambient pressure (100 kilo-pascal (kPa) at sea level; 85 kPa at 1500 meters of altitude), with whatever the ambient air composition is, including humidity. A series of evacuation and fill cycles can then be performed, with the cycles performed so as to warm the product.

Each evacuation will result in a temperature drop. For example, reducing the pressure in the chamber from 100 kPa to 50 kPa would reduce the temperature of the gas in the chamber (according to Gay-Lussac's Law and/or the Third Gas Law) from 294 K (21 C) to 147 k (−126 C), assuming instantaneous withdrawal. By drawing the gas out slowly, however, the gas remaining in the chamber will interact with chamber walls to limit temperature drop. For example, the chamber walls may be at room temperature or may be warmed by external circulating fluid or by the use of resistive heating, to limit actual cooling within the chamber during evacuation. Thus, in an example, the pressure drop may occur over a period of one to three minutes, or more or less, for example. Optionally, there may be a low pressure/temperature dwell period which follows, for example, of one to three minutes.

Next, re-pressurization is performed, in some examples after allowing the temperature in the chamber to return to room temperature. Re-pressurizing from 50 kPa to 100 kPa would cause the temperature in the chamber to increase from 294 K (21 C) to 588 K (315 C), if done instantly, though it is more likely to take several seconds. In an example, the re-pressurizing step can be performed more quickly than the depressurization step, such as in a matter of seconds using a pressurized gas source, though this need not be the case. The injected gas may be dry air, if desired, though other materials may be used. Injected gas may be warmed itself, if desired. Optionally, after gas injection, the chamber may be placed in a short dwell, for example, of 2-5 minutes, or more or less, before repeating the cycle.

While gas in the chamber may be cooled or heated to rather extreme temperatures during these steps (less than −100 C, to more than 300 C), the product itself will not reach such extremes. The rate of heat transfer by convection is directly proportional to the temperature difference between the object being heated and the fluid or gas used in heating. By performing re-pressurization as described, a large temperature difference is created, making the convection heat transfer faster. However, the mass of air in the chamber will typically be much less than the mass of the product being pre-treated.

This cycle may be repeated for a quantity of cycles. For purposes of a validated sterilization procedure, the quantity of cycles can be fixed once tested. For example, in a 1600 L chamber holding a pallet of about 5000 pre-filled syringes in Tyvek packaging each having a mass of about 20 g each, inclusive of individual packaging for each syringe, the total mass of the product to be warmed and sterilized would be about 100 kg. At ambient pressure and temperature, the chamber would hold just under 2 kg of air. Moreover, the specific heat of dry air will be less than the specific heat of the packaging, syringe, and syringe contents by factors in the range of 1.5 to 4 or more. As a result, the cycling itself cannot be expected to quickly warm the product in a way that risks any overheating.

The effect of the cycling can be understood using standard calorimetry:

$$(c_1 \times m_1 \times \Delta T_1)_{dry\ air} = -(c_2 \times m_2 \times \Delta T_2)_{product}$$

Where $c_1$ is the specific heat of the in-chamber air, $m_1$ is the mass of in-chamber air, $\Delta T_1$ is the temperature change of the in-chamber air, $c_2$ is the specific heat of the product, $m_2$ is the mass of the product, and $\Delta T_2$ is the temperature change of the product. Treating $c_2$ as 2 kj/kg*K, and using the above introduced example for mass, at ambient pressure:

$$\left(1\ kj/\text{kg} * K \times 1\ \text{kg} \times \Delta T_1\right) = -\left(2kj/\text{kg} * K \times 100\ \text{kg} \times \Delta T_2\right)$$

$$\Delta T_1 = -200 \times \Delta T_2$$

Using the above example of pressure cycling between 100 kPa and 50 kPa, with ambient temperature of 294 K (21 C), the $\Delta T_1$ variable would be 294 K, and if the chamber walls absorbed no heat at all, each cycle should change the temperature of the product by about 1.5 K. However, the chamber walls will absorb heat as well, and the actual effect of each warming cycle will be significantly less. Because the chamber walls are typically metal, with a higher heat conductivity than the syringe packaging and the syringe itself, a majority of the heating effect may be absorbed by the chamber walls.

For the low-pressure portion of the cycle, assuming the low pressure stage occurs at 50 kPa, the mass of air would be reduced in half, and the other parameters can be treated as constant, so:

$$\Delta T1 = -400 \times \Delta T2$$

Here, the $\Delta T1$ variable would be 147 K. Thus the cooling effect would be in the range of 0.4 K. Again, the actual impact is muted by the absorption of heat from the chamber walls which additionally have a higher heat conductivity than the syringe and/or packaging in many installations. More importantly, the cooling effect would be less than the heating effect. The use of a non-metal chamber wall may provide more thermal isolation to the chamber contents, if desired, as could the use of a heated chamber wall.

While it is not necessary to keep the pressure below ambient during such cycling, this may be desirable. Some sterilization chambers are built with the assumption that internal pressure of the sterilization chamber will not exceed ambient pressures if, for example, the sterilant to be used is one that should not be allowed to escape the sterilization chamber (true of most chemical sterilant products). For such chambers, it may be desired to keep the pressure below ambient during any process to avoid stressing chamber seals, walls, etc.

If, on the other hand, a chamber is designed for increased pressures, it may be possible to further accelerate the warming process by pressurizing the chamber above ambient, if desired. For example, the pressure cycle may be from 100 kPa to 150 kPa; while the temperature variation in such a cycle may be less than the above example of 50 kPa and 100 kPa, the mass of air in the chamber will be greater, increasing heat transfer.

Some products may be sensitive to low pressures under, for example, 50 kPa, or 30 kPa. For example, low pressures of 30 kPa or lower may place a pre-filled syringe at risk of barrel/plunger movement. Thus the process may be limited to using pressures above 30 kPa, depending on the particular chamber, product, etc. This lower limit may not apply to some products, however.

Several more specific examples follow. Except for that discussed in association with FIG. 5, these are prophetic examples. The sterilization chamber may be filled with dry air in the described examples. The time required may be reduced by introducing humidity into the chamber, with the amount of humidity remaining low enough that the low pressure portion of each cycle occurs with a relative humidity of less than about 95%, or less than about 80%, or some other upper limit, to avoid or prevent condensation.

Example 1:

A pallet of product to be sterilized is removed from refrigeration, and secondary packaging (plastic wrap) of the pallet is removed. The pallet is placed in a sterilization chamber. Inside the sterilization chamber, air is circulated using a blower. No pressure cycling is performed.

It is expected that this approach would reduce the time needed for the product to reach room temperature (20 C) from a chilled condition (5 C) to about 24 hours, as compared to 72 hours that is common using passive warming with plastic wrap in place.

Example 2:

A pallet of 100 kg of product to be sterilized is removed from refrigeration, and secondary packaging (plastic wrap) of the pallet is removed. The pallet is placed in a sterilization chamber with a 1000 L volume. Inside the sterilization chamber, air is circulated using a blower. Pressure cycling is performed as follows:

With the chamber walls at ambient/room temperature (20 C), the chamber is sealed. Next, 50 cycles as follows are performed:

- Over the course of 1 minute, pressure is reduced to 75 kPa from ambient (100 kPa).
- The chamber dwells at 75 kPa for 1 minute
- Over the course of 10 seconds, pressure is increased to 100 kPa
- The chamber dwells at 100 kPa for 2 minutes and 50 seconds The 50 cycles each take 5 minutes, meaning four hours and ten minutes of cycling takes place. The product is then left in the chamber with room temperature air circulating into and out of the chamber. It is expected that this approach would reduce the time needed for the product to reach room temperature (20 C) from a chilled condition (5 C) to about 18 hours.

Example 3:

A pallet of 100 kg of product to be sterilized is removed from refrigeration, and secondary packaging (plastic wrap) of the pallet is removed. The pallet is placed in a sterilization chamber with a 1000 L volume, and the chamber is sealed. Inside the sterilization chamber, air is circulated using a blower. Pressure cycling is performed with the chamber walls warmed to 35 C by the use of a circulating fluid passing through pipes thereon. 50 cycles as follows are performed:

- Over the course of 2 minutes, pressure is reduced to 50 kPa from ambient (100 kPa).
- The chamber dwells at 50 kPa for 1 minute
- Over the course of 15 seconds, pressure is increased to 100 kPa
- The chamber dwells at 100 kPa for 3 minutes and 45 seconds The 50 cycles each take 7 minutes, meaning five hours and fifty minutes of cycling takes place. The product is then left in the chamber with room temperature air circulating into and out of the chamber, and the circulating/warming fluid in the chamber walls is stopped. It is expected that this approach would reduce the time needed for the product to reach room temperature (20 C) from a chilled condition (5 C) to about 12 hours.

The above cycles may use dry air or humidity may be added. In some examples, humidity may be introduced during initial portions of the cycling and later removed. Doing so may serve to start the sterilization procedure in a known state. Alternatively, initial cycles may be performed to dry the product and sterilization chamber, and humidity is then added in a controlled fashion, again placing the chamber in a known state. In some examples, the product to be sterilized may be complex, for example, comprising multiple materials and structures which yield an inhomogeneous response to temperature changes. As a result, it may be advisable to allow a resting period prior to initiation of the sterilization cycle to allow temperature equilibration of the product to be sterilized. This need not be the case, however.

Rather than injecting humidity, other gasses may be used. For example, helium or hydrogen gas have relatively high specific heats and may be used, to the extend such gasses can be tolerated by the product to be sterilized and/or chamber equipment.

The above examples assume that the pressure is increased to ambient only. In other examples, pressure may be still further increased, above ambient pressures, if desired, and as limited by the capabilities of the sterilization chamber to hold elevated pressures and the ability of the product to be sterilized to withstand elevated temperatures.

It should be noted that in each of these examples, the air temperature is allowed to increase well above a temperature that the sterilization products could in fact withstand if actually heated to such temperatures. However, as noted, the mass and specific heat of the in-chamber gas (whether dry air or humidified air) are much less than the mass and specific heat of the products in the chamber. As a result, harm to the product from overheating is unlikely. In some examples, the chamber walls may be warmed to relatively mild temperatures, in the range of up to 50 C, for example, though higher temperatures may be used, as desired.

A temperature sensor, or plurality of temperature sensors, may be provided in or on the product sample(s) to monitor progress of the warming procedure. Such additional sensor(s) may also be used for process monitoring. Such sensors may be removed prior to sterilization or left in place, as desired.

Figure 3:
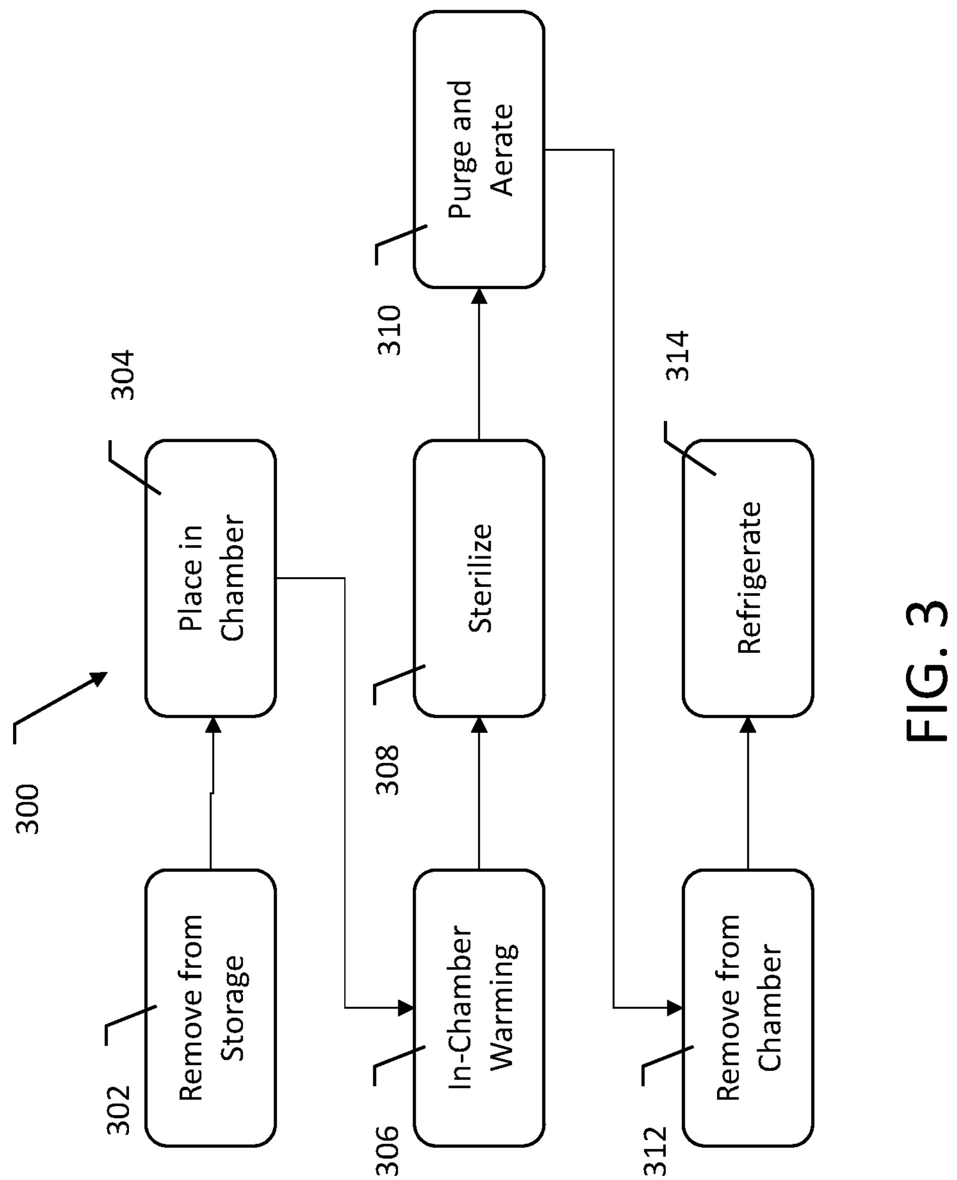
FIGS. 3 and 4 show illustrative sterilization processes.

FIG. 3 provides an illustrative example of a method at 300. Here, the product to be sterilized is removed from refrigerated storage at 302 and placed in the sterilization chamber 304 while still cold. Next, the product to be sterilized is warmed in the chamber, as indicated at 306. Warming at 306 may be performed using in-chamber air circulation alone or combined with one or more of pressure cycling and/or warming the chamber walls. Once the product is warmed to a suitable temperature, sterilization is performed as indicated at 308. The chamber is then purged and aerated at 310, the product is removed from the chamber at 312, and the product is then refrigerated as indicated at 314.

Figure 4:
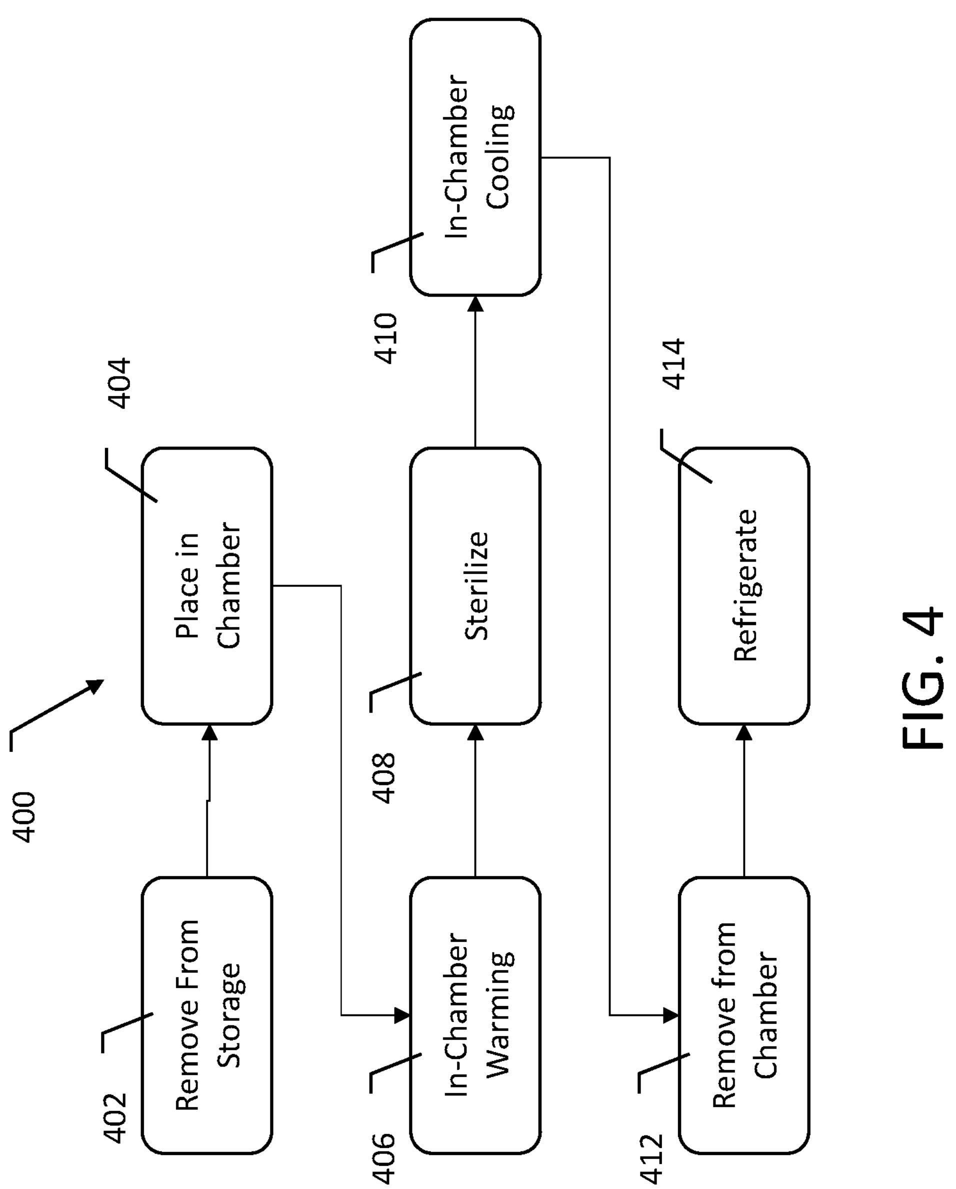

In some examples, the sterilization chamber processes may also be used to begin cooling product after it has been sterilized. Typically the product, once sterilized, is aerated for one or more hours, with air cycled through the sterilization chamber to remove residual chemicals from the sterilization process. During this time, pressure cycling and/or chamber wall cooling may be used to cool the product, if desired. FIG. 4 shows an example.

In FIG. 4, the method 400 again begins with removing the product to be sterilized from storage, as indicated at 402, and placing the product 404 in the sterilization chamber as indicated at 404. Next, optionally, in-chamber warming is performed at 406. The product is sterilized as indicated at 408. Once the sterilization procedure is completed, in-chamber cooling is performed. In an example, the sterilization chamber walls may be cooled by circulating a cooling fluid therethrough, such as by circulating a fluid at a temperature below room temperature, at 2 C, or lower, such as at −10 C, or still colder, if desired and within the tolerances of the equipment. A blower or air circulator in the chamber can be used to circulate air within the chamber to enhance the cooling effect. The cooling effect may be enhanced further by the inclusion of gas constituents with higher heat capacities, to the extent such constituents are well tolerated in the system and by the sterilized product.

Pressure cycling may be performed as part of the in-chamber cooling 410. For example, pressure is reduced from an ambient pressure to a lower, target pressure, which as described above will cause the air in the chamber to cool rapidly in proportion to the change in pressure. When cooling 410, the pressure reduction can occur quickly, such as over the course of a few seconds, rather than doing so slowly. The product can then dwell at the reduced pressure for several minutes, and pressure can be allowed to return slowly to ambient, such as over the course of a minute or more. This cycle of quick pressure reduction, dwell and slow pressure increase can be performed repeatedly, as desired. Each time the chamber is evacuated, the air in the chamber is being removed, which is necessary to the aeration process in any event. Thus the product in the chamber can be cooled at block 410 until aeration is completed and the product is removed from the chamber 412 and returned to refrigerated storage at 414. Because the depressurization includes removing air from the chamber, it may be that cooling starts as part of the completion of the sterilization procedure 408.

Figure 5:
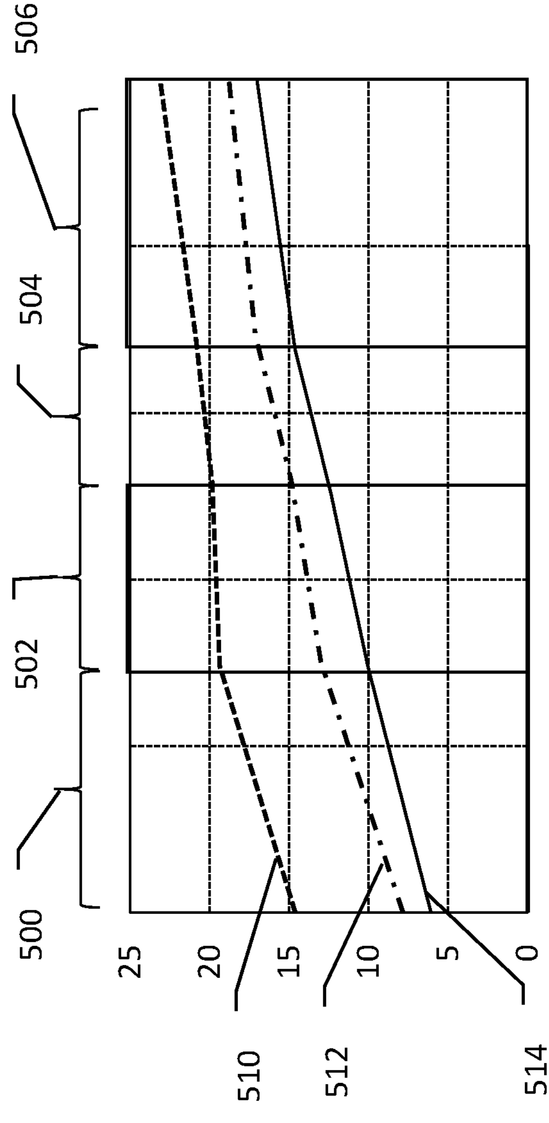
FIG. 5 is a graph of results of a test.

FIG. 5 is a graph of results of a test run. In this test, a pallet of pre-filed syringes in Tyvek packaging was placed in a sterilization chamber after being removed from cold storage (6 C). Several phases of warming were used to raise the product to room temperature (approximately 21 C). The Y-axis shows time in minutes from the start of pressure cycling in the first phase 500. The X-axis shows the temperature reported by temperature sensors in the pallet, as follows: outside temperature 510 is the output of a temperature sensor at the outer portion of the pallet, middle temperature 512 is the output of a temperature sensor placed about halfway between the outside of the pallet and the center of the pallet, and center temperature 514 is the output of a temperature sensor placed in the center of the pallet. The pallet had been removed from cold storage for over an hour prior to the cycling, and external wrapping had been removed from the pallet as well. As a result, the pallet was no longer at its coldest, and it can be seen that the outside temperature 510 was already at about 15 C, though the center temperature 514 remained near the cold storage temperature of about 6 C during that hour, demonstrating a problem with passively warming the pallet—product at the outside of the pallet would substantially warm to room temperature long before the center of the pallet could do the same.

The first phase 500 lasts for about 110 minutes. Pressure was reduced and increased in a cycle from 100 kPa (ambient) down to 75 kPa, and back again, with a pressure change starting each minute on the minute, using dry air, during the first phase. The chamber blower was on throughout the first phase 500. The chamber walls were allowed to reside at room temperature; no heating or cooling was applied to control wall temperature.

The second phase 502 provides a way of determining differences between simply resting at room temperature and the pressure cycling process, and lasts about 80 minutes. No pressure cycling was performed in the second phase 502, and the blower was off.

The third phase 504 lasts about 60 minutes. Pressure was reduced and increased in a cycle from 100 kPa (ambient) down to 75 kPa, and back again, with a pressure change starting each 30 seconds, using ambient/room air (having some humidity). The chamber blower was on throughout the third phase 504. The chamber walls were allowed to reside at room temperature; no heating or cooling was applied to control chamber wall temperature. It is expected that using room air, rather than dry air, would cause a larger warming effect due to the higher heat capacity of humid air over that of dry air.

The fourth phase 506 lasts about 110 minutes. No pressure cycling was performed in the fourth phase 506, and the blower was off.

To judge the impact of the different operations in each phase, the slope of temperature versus time was calculated for each of the three sensor positions and each of the four phases, yielding results as follows:

TABLE 1

| | Phase 1 500 | Phase 2 502 | Phase 3 504 | Phase 4 506 |
|---|---|---|---|---|
| Outside Sensor 510 | 0.0327 | 0.0045 | 0.0125 | 0.017 |
| Middle Sensor 512 | 0.0433 | 0.0263 | 0.0301 | 0.014 |
| Center Sensor 514 | 0.0323 | 0.0269 | 0.0305 | 0.0179 |

The slopes in Table 1 are based on best fit lines calculated for each phase. The middle and center sensors show that the increase in temperature per unit time is greater with the colder parts of the load when using the pressure cycling. The effect of using room air, which has some humidity, rather than dry air, is difficult to identify in this test due to the effect of increased temperature of the load from phase 1 to phase 3; that is, the slope of change is expected to reduce as the temperature of the load gets closer to room temperature, offsetting the effect of increased heat capacity of the more humid air. Regardless of the process noise present in this actual test with actual product, it can be observed that the pressure cycling in the first phase 500 and third phase 504 increased the rate at which product, including the product toward the center of the load, warmed, providing proof of concept.

Various pressure cycling parameters may be used. In illustrative examples, pressure may cycle between about 100 kPa and about 75 kPa; between about 100 kPa, and about 75 kPa; between about 100 kPa and about 50 kPa; between about 75 kPa and about 50 kPa; between about 125 kPa and about 100 kPa; between about 150 kPa and about 100 kPa; between about 125 kPa and about 75 kPa; and/or between about 150 kPa and about 75 kPa.

The following are some illustrative examples. Each of these non-limiting examples can stand on its own, or can be combined in various permutations or combinations with one or more of the other examples.

A first illustrative and non-limiting example takes the form of a method of sterilizing a product comprising: removing the product from cold storage; placing the product in a sterilization chamber while the product remains below room temperature; warming the product in the sterilization chamber; and sterilizing the product in the sterilization chamber.

Additionally or alternatively, the sterilization chamber includes an air circulation device, and the step of warming the product comprises activating the air circulation device. Additionally or alternatively, the method may include warming air passing through the air circulation device.

Additionally or alternatively, the sterilization chamber includes a sterilization chamber wall having warming means associated therewith, and the step of warming the product comprises activating the warming means to warm the sterilization chamber wall. The warming means may include a resistive or other heating element coupled to the chamber, or placed in a circulating airstream, or one or more pipes for circulating a fluid within or along the chamber walls.

Additionally or alternatively, the step of warming the product comprises cycling pressure for warming within the sterilization chamber between a first pressure and a second pressure, the second pressure being lower than the first pressure. Additionally or alternatively, cycling pressure for warming comprises: reducing pressure over a first period of time from the first pressure to the second pressure; dwelling at the second pressure for a second period of time; increasing pressure over a third period of time from the second pressure to the first pressure; and dwelling at the first pressure for a fourth period of time. Additionally or alternatively, the first period of time is longer than the third period of time.

Additionally or alternatively, the method may further comprise, after sterilizing the product, cooling the product in the sterilization chamber.

Additionally or alternatively, the sterilization chamber includes a sterilization chamber wall having cooling means associated therewith, and the step of cooling the product comprises activating the cooling means to cool the sterilization chamber wall.

Additionally or alternatively, the step of cooling the product in the sterilization chamber comprises cycling pressure for cooling in the sterilization chamber between a third pressure and a fourth pressure, the fourth pressure being less than the third pressure.

Additionally or alternatively, cycling pressure for cooling comprises: reducing pressure over a fifth period of time from the third pressure to the fourth pressure; dwelling at the fourth pressure for a sixth period of time; increasing pressure over a seventh period of time from the fourth pressure to the third pressure; and dwelling at the third pressure for an eighth period of time. Additionally or alternatively, the fifth period of time is shorter than the seventh period of time. Additionally or alternatively, the sterilization chamber includes an air circulation device, and the step of cooling the product comprises activating the air circulation device and cooling air passing through the air circulation device.

Additionally or alternatively, the second pressure is an ambient pressure, and the first pressure is higher than ambient pressure. Additionally or alternatively, the first pressure is about 100 kPa, and the second pressure is about 75 kPa. Additionally or alternatively, the first pressure is about 100 kPa, and the second pressure is about 50 kPa. Additionally or alternatively, the first pressure is about 75 kPa, and the second pressure is about 50 kPa. Additionally or alternatively, the first pressure is about 125 kPa, and the second pressure is about 100 kPa. Additionally or alternatively, the first pressure is about 150 kPa, and the second pressure is about 100 kPa. Additionally or alternatively, the first pressure is about 125 kPa, and the second pressure is about 75 kPa. Additionally or alternatively, the first pressure is about 150 kPa, and the second pressure is about 75 kPa.

Additional illustrative and non-limiting examples take the form of systems for sterilization of products comprising controllers, such as a system as in FIG. 1, described above. Within such systems, a control and monitoring block 104 may comprise machine readable memory media having instructions thereon for performing any of the warming and sterilizing steps, the sterilization and cooling steps, and/or the combined sequence of warming, sterilizing, and cooling steps. Still further examples may perform the above methods for in-line sterilization, and/or may have in-line sterilization systems that include controllers configured as just described.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A method of sterilizing a product comprising:

removing the product from cold storage;

placing the product in a sterilization chamber while the product remains below room temperature;

warming the product in the sterilization chamber by cycling pressure, in a warming cycle, within the sterilization chamber between a first pressure and a second pressure, the second pressure being lower than the first pressure, the cycling pressure including:

reducing pressure over a first period of time from the first pressure to the second pressure;

dwelling at the second pressure for a second period of time;

increasing pressure over a third period of time from the second pressure to the first pressure; and dwelling at the first pressure for a fourth period of time; and sterilizing the product in the sterilization chamber, wherein the first period of time is longer than the third period of time.

2. The method of claim 1 wherein the sterilization chamber includes an air circulation device, and the step of warming the product comprises activating the air circulation device.

3. The method of claim 2, further comprising warming air passing through the air circulation device.

4. The method of claim 1, wherein the step of warming the product comprises warming the sterilization chamber wall.

5. The method of claim 1 further comprising, after sterilizing the product, cooling the product in the sterilization chamber.

6. The method of claim 5, wherein the step of cooling the product comprises cooling the sterilization chamber wall.

7. The method of claim 5, wherein the step of cooling the product in the sterilization chamber comprises cycling pressure for cooling in the sterilization chamber between a third pressure and a fourth pressure, the fourth pressure being less than the third pressure.

8. The method of claim 7 wherein cycling pressure for cooling comprises:

reducing pressure over a fifth period of time from the third pressure to the fourth pressure;

dwelling at the fourth pressure for a sixth period of time;

increasing pressure over a seventh period of time from the fourth pressure to the third pressure; and dwelling at the third pressure for an eighth period of time.

9. The method of claim 8 wherein the fifth period of time is shorter than the seventh period of time.

10. The method of claim 5, wherein the sterilization chamber includes an air circulation device, and the step of cooling the product comprises activating the air circulation device and cooling air passing through the air circulation device.

11. The method of claim 1, wherein the second pressure is an ambient pressure, and the first pressure is higher than ambient pressure.

12. The method of claim 1, wherein the first pressure is about 100 kPa, and the second pressure is about 75 kPa.

13. The method of claim 1, wherein the first pressure is about 100 kPa, and the second pressure is about 50 kPa.

14. A sterilization system comprising:

a sterilization chamber configured to contain a product, the sterilization chamber including:

a sterilant source configured to communicate a sterilant into the sterilization chamber, the sterilant configured to sterilize the product;

a vacuum source configured to adjust pressure in the sterilization chamber; and a blower configured to circulate air in the sterilization chamber; and a control and monitoring system for controlling conditions in the sterilization chamber, the control and monitoring system configured to perform a method comprising:

warming the product in the sterilization chamber by cycling pressure within the sterilization chamber between a first pressure and a second pressure via the vacuum source, the second pressure being lower than the first pressure, the cycling pressure including:

reducing pressure over a first period of time from the first pressure to the second pressure via the vacuum source;

dwelling the sterilization chamber at the second pressure for a second period of time;

allowing gas to enter sterilization chamber to increase pressure over a third period of time from the second pressure to the first pressure, the first period of time longer than the third period of time; and dwelling at the first pressure for a fourth period of time; and sterilizing the product in the sterilization chamber using the sterilant source.

15. The system of claim 14, wherein the control and monitoring system is configured to perform the step of warming the product by warming the sterilization chamber wall while the pressure is cycled between the first pressure and the second pressure.

* * * * *